(12) United States Patent
Tuma

(10) Patent No.: US 7,883,545 B2
(45) Date of Patent: Feb. 8, 2011

(54) METHOD AND DEVICE FOR DETERMINING THE CHANGE IN AN OBJECT

(75) Inventor: Gregor Tuma, Münich (DE)

(73) Assignee: BrainLAB AG, Feldkirchen (DE)

( * ) Notice: Subject to any disclaimer, the term of this patent is extended or adjusted under 35 U.S.C. 154(b) by 480 days.

(21) Appl. No.: 11/857,551

(22) Filed: Sep. 19, 2007

(65) Prior Publication Data

US 2008/0077052 A1   Mar. 27, 2008

Related U.S. Application Data

(60) Provisional application No. 60/827,510, filed on Sep. 29, 2006.

(30) Foreign Application Priority Data

Sep. 21, 2006  (EP) .................................. 06019756

(51) Int. Cl.
*A61F 2/30* (2006.01)
*A61B 5/103* (2006.01)
(52) U.S. Cl. ..................... 623/23.39; 600/587
(58) Field of Classification Search ................ 600/595; 606/102; 623/23.39
See application file for complete search history.

(56) References Cited

U.S. PATENT DOCUMENTS

| 6,692,447 | B1 | 2/2004 | Picard |
| 2003/0153829 | A1 | 8/2003 | Sarin et al. |
| 2003/0181920 | A1* | 9/2003 | Hawkins et al. ............. 606/102 |
| 2004/0171924 | A1* | 9/2004 | Mire et al. .................. 600/407 |
| 2004/0171929 | A1* | 9/2004 | Leitner et al. ............... 600/424 |
| 2006/0064109 | A1* | 3/2006 | Iversen ....................... 606/102 |
| 2006/0161079 | A1* | 7/2006 | Choi et al. .................. 600/595 |
| 2006/0217737 | A1* | 9/2006 | Iversen ....................... 606/102 |
| 2009/0125177 | A1* | 5/2009 | Tanaka et al. ................. 701/29 |

FOREIGN PATENT DOCUMENTS

| EP | 1 563 810 | 8/2005 |
| EP | 1 654 997 | 5/2006 |

* cited by examiner

*Primary Examiner*—Bruce E Snow
*Assistant Examiner*—Melissa Hoban
(74) *Attorney, Agent, or Firm*—Renner, Otto, Boisselle & Sklar, LLP

(57) ABSTRACT

A method is provided for determining a dimensional change in a first object, wherein in an initial state said first object is connected to a second object via a joint, and wherein a first reference system is rigidly connected to the second object. The method includes using a non-invasive coupling device to couple a second reference system to the first object; ascertaining and/or storing a first location corresponding to a location of the second reference system relative to the first reference system, and a second location corresponding to a location between at least one reference point on the first object relative to the first reference system; separating the first object from the second object at the joint; altering the first object; re-assembling the altered first object and the second object to form the joint, wherein the first location is used to align the altered first object to the second object; after alignment, ascertaining or storing a third location corresponding to a location of the at least one reference point relative to the first reference system; and determining the dimensional change in the first object due to the alteration based on a change in location between the second location and the third location of the at least one reference point.

9 Claims, 2 Drawing Sheets

METHOD AND DEVICE FOR DETERMINING THE CHANGE IN AN OBJECT

RELATED APPLICATION DATA

This application claims priority of U.S. Provisional Application No. 60/827,510 filed on Sep. 29, 2006, which is incorporated herein by reference in its entirety.

FIELD OF THE INVENTION

The present invention relates to a method and device for determining a change in an object, such as a change in the length of the object. More particularly, the invention relates to determining a change in a first object that at one time was connected to a second object and, once detached from the second object, the first object was manipulated before being reconnected to the second object.

BACKGROUND OF THE INVENTION

When performing a joint replacement, it should be ensured that the reconstructed joint provides motion substantially the same as the original joint. For example, in a hip joint replacement, a portion of the hip and/or of the femur may be replaced with artificial components (the hip socket and/or femoral head may be replaced with an artificial parts). After the implant has been performed, the alignment and range of motion of the artificial joint should mimic that of the original joint.

In order to determine the relative position between the femur and the hip and, thus, quantify changes in the length of the femur after an implantation of the artificial components, it is known to directly attach a reference star to the pelvic bone and the femur (e.g., attaching the reference star directly to the respective parts using screw fasteners). Then by monitoring the movement of the reference stars as the joint is exercised through normal movement, the trajectory and range of motion can be ascertained and changes in length can be determined.

SUMMARY OF THE INVENTION

In order to detect a change (e.g., a change in length) of a first object, wherein in an initial state the first object is connected to a second object via a joint such as a ball joint (e.g., a femur attached to a hip via a hip joint), a first reference system (e.g., a reference star or other array including passive (reflective) or active markers) can be connected (preferably directly connected via screw fasteners) to the second object (e.g., the pelvic bone) in the initial state. A second reference system, such as second reference star, can be connected to the first object, wherein the second reference system is not directly connected to the first object. Instead, the second reference system can be attached to the first object, for example, by means of an elastic belt in the immediate vicinity of the first object (e.g., attached to a mantle that surrounds the first object).

In other words, the second reference system can be fixed by the belt, wherein the belt is placed around a region of the upper leg so as to hold the second reference system in a substantially fixed position in relation to the surface of the skin. It is thus not necessary to fasten the second reference system directly to the femur, for example by means of a pin, such that a surgical incision at this point can be omitted.

Before the joint is taken apart, at least one reference point is detected or identified on the second object, e.g., on the femur. The at least one reference point can be detected or identified using a pointer that includes markers (e.g., passive or active markers) attached thereto, wherein a navigation system can determine a location of the pointer in three-dimensional space based on the markers. The pointer can be moved to the reference point (e.g., a landmark or marked region) in a known way to acquire a location of the reference point, and the location of the reference point, as well as a location of the first and second reference system relative to the reference point, then can be stored for later use (e.g., during reassembly of the joint). Thus, using a medical navigation system, the pointer can be used to identify or detect the spatial position of the reference point.

The connection between the two objects then can be released to enable work on the second and/or first object to be performed. For example, work may be performed on the femur, wherein a length of the femur is changed (e.g., a damaged femoral head may be removed and an implant attached to the remaining portion of the femur). If the two objects (e.g., the femur including the implant (femoral head) and the pelvic bone) are to be reassembled, or the attached implant is to be verified with respect to its shape or location, then it is important to know the precise geometry (e.g., length) of the object that has been changed such that, for example, the reassembled joint differs as little as possible from the healthy joint or from the positional relationship of the two joint portions relative to each other before the procedure.

Using the second reference system, the first object can be moved to a position that roughly corresponds to the position in the initial state. However, since the second reference system is not directly and rigidly connected to the first object, the position of the first object may not exactly correspond to the initial position. To compensate for this possible error, the position of the previously detected at least one reference point is detected again to precisely position and thus exactly align the first object relative to the second object, wherein a known pointer as described above can be used to detect the reference point.

It is not necessary, however, for the pointer to be moved to the same reference point. If the position of a second reference point relative to the first reference point is known, the pointer may be moved to the second reference point on the second object. The second reference point, for example, can be a second landmark having a known arrangement relative to the previously detected first reference point, or can be any other point having a known distance in relation to the previously detected first reference point.

Once the first object has been precisely positioned to correspond to the initial state, a change in position of a present location of the reference mark with respect to the initial location of the reference mark can be detected (e.g., a change in position relative to the first reference system). The change in the reference point then can be used to establish a change in length and/or orientation of the first object with respect to the initial condition.

Thus, it is possible to detect or measure the length of the bone or leg and an offset of a joint portion using a less invasive method of attaching at least one reference system (e.g., at least one reference system is attached to the patient using a non-invasive attachment method). As used herein, a non-invasive attachment method is any attachment method that does not destroy or damage the object to which the device is attached. For example, cutting into tissue and/or drilling or screwing into bone matter are examples of invasive attachment methods. Non-invasive attachment methods include, for example, attachment via a belt or elastic member.

Determination of the length is important, particularly in hip operations (total hip arthroplasty: THA), since after implanting an artificial hip joint or hip joint portion, the length is used to find the desired alignment or relative position between the two joint portions (e.g., the pelvic bone comprising the hip joint cavity and the femoral head).

Also provided herein is a computer program that, when it is loaded onto a computer or is running on a computer, performs one or more of the method steps described above, and a program storage medium or computer program product comprising such a program.

A device is provided for determining the change, in particular the change in length, of a first object that in an initial state is connected to a second object via a joint, wherein a first reference system is fastened directly and preferably fixedly to the second object, and a second reference system is not directly connected to the first object but instead is indirectly attached to the first object or attached in a vicinity of the first object, preferably with only a very small capacity to shift on the first object, and a pointer instrument or pointer is provided for determining a position of at least one reference point. A navigation system for detecting positions of the first reference system, the second reference system and/or the pointer also is included. By comparing the detected positions in an initial state in which the joint is still connected or assembled with the detected positions after the first and/or second object has been changed, the change in length of the second object can be detected, wherein it is also possible to quantitatively ascertain how large said change in length is, e.g., whether a bone comprising an attached implant exhibits the correct length or is too long or too short.

BRIEF DESCRIPTION OF THE DRAWINGS

The forgoing and other features of the invention are hereinafter discussed with reference to the drawing.

DETAILED DESCRIPTION

Figure 1:
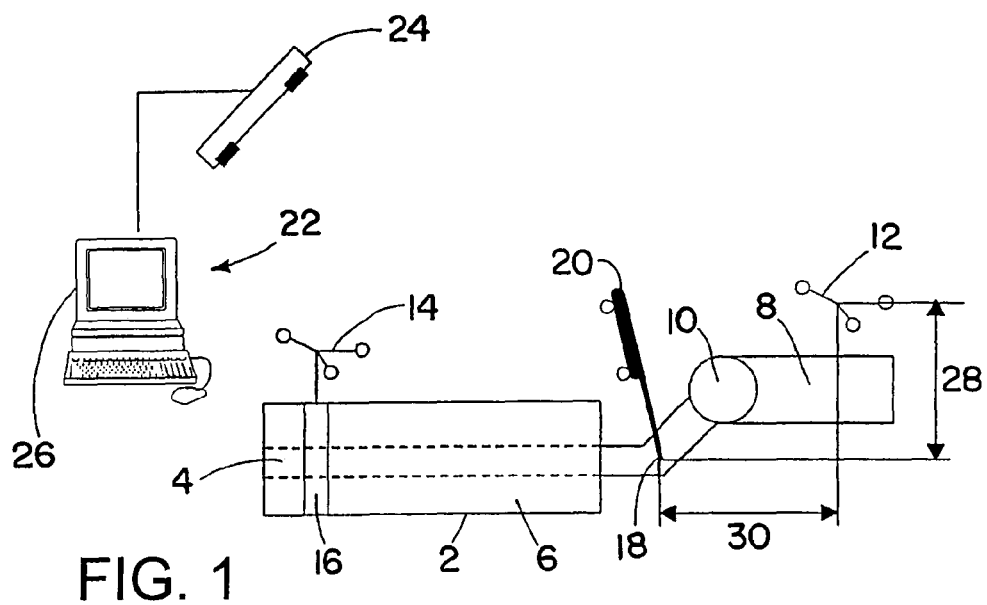
FIG. 1 is a schematic representation of an exemplary hip joint in the initial state, before an implant is attached onto the femur.

FIG. 1 illustrates an exemplary upper leg as an elongated object 2, comprising a femur or upper leg bone as a solid core 4, around which tissue such as, for example, skin and/or muscle is arranged as an elastic mantle 6. The object 2 is connected by the core 4 to a second object 8 by means of a ball joint 10. A reference star or marker array 12 is provided on the second object 8 as a first reference system, fixedly connected to said second object 8, in order to determine or establish a coordinate system. A second reference system 14 is provided on the mantle 6 of the first object 2, for example by means of a belt 16 around the mantle 6. The mantle 6 and/or the belt 16 can be moved relative to the rigid or fixed core 4 when, for example, the object 2 is moved. The reference system 12 of the second object 8, however, remains fixedly or rigidly connected to the second object 8, even when it is moved.

A reference point 18 on the core 4 of the first object 2 is detected by means of a pointer 20 on which, as also with the reference system 12 and 14, reflective markers are provided.

The positions of the first reference system 12, the second reference system 14 and the pointer 20 can be detected by means of a known navigation system 22, which, for example, comprises infrared cameras 24 and a computer system 26. If the position of the reference system 12 is known, then, for example, after a known registration of an image data set (for example CT) of the second object 8, the spatial position of the second object 8 (which, for example, also can serve as a reference system similar to that of the reference system 12) can be determined.

In the initial state shown in FIG. 1, the location of the second reference system 14 relative to the first reference system 12 and the location of the reference point 18, detected by means of the pointer 20, relative to the first reference system 12 can be detected and stored by means of the navigation system 22. This data can be used to define an initial state or relative positional relationships that should be reinstated after the surgical procedure has been completed. It is possible to ascertain, for example, in relation to the first reference system 12, the height 28 and distance 30 of the reference point 18.

Figure 2:
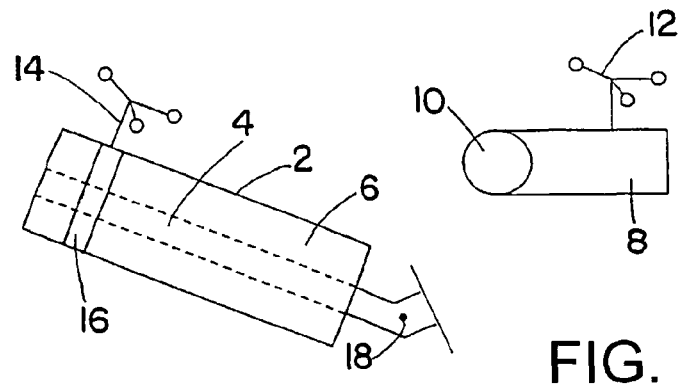
FIG. 2 is a schematic representation of the hip joint shown in FIG. 1 after the joint connection has been released and the femoral head removed.

FIG. 2 shows the joint 10 of FIG. 1, after the joint connection between the first object 2 and the second object 8 has been released. As can be seen from the schematic representation in FIG. 2, the joint portion of the first object 2 has been cut off from the core 4 or femur and replaced with an artificial joint head 4' (e.g., a prosthesis).

Figure 3:
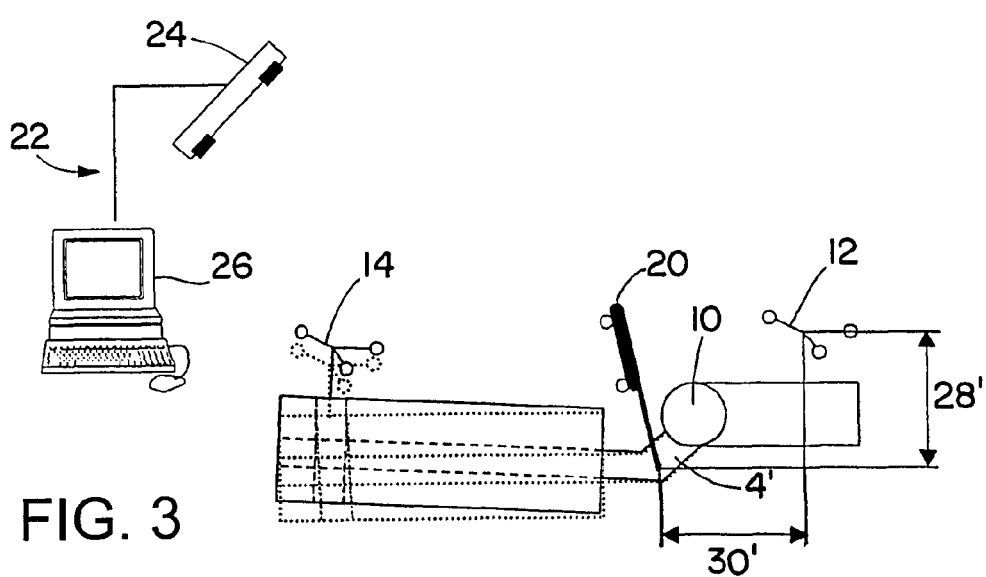
FIG. 3 is a schematic representation of the hip joint of FIGS. 1 and 2 after a femoral head implant has been attached and the joint components assembled.

Once the artificial joint head 4' has been placed onto the core 4 of the first object 2, the latter has to be correctly positioned relative to the second object 8 in order to re-establish the (ball) joint connection in the initial state shown in FIG. 1, with the correct positional relationship. However, in the state shown in FIG. 3, the change in the length or geometry and the exact position of the first object 2 are not exactly known, for example, due to possible slippage of belt 16.

In order to measure the change in geometry after the core 4 of the first object 2 has been cut, the previously detected reference or marker point 18 on the core 4 of the first object 2, as well as detected positions of the reference systems 12 and 14 can be used. More specifically, the second reference system 14 connected to the first object 2, with the aid of the navigation system 22, can be used to approximately relocate and position the two objects relative to each other (e.g., the rotational degrees of freedom of the object 2 relative to object 8 are approximately set in the same way as the initial location defined by the user (before the objects were separated)). As noted above, this initial location was made known to the navigation system 22 and stored therein as a reference for such subsequent repeat measurements (e.g., to position the first object 2 relative to the second object 8). Due to the possible relative movement between the second reference system 14 and the first object 2, the first object 2 can only be aligned or positioned with respect to the three rotational degrees of freedom.

Once the two objects 2 and 8 have been reconnected on the ball joint 10, the rotational degrees of freedom are adjusted such that the original orientation can be found within a certain tolerance limit. This tolerance limit depends on the change in the relative location of the second reference system 14 relative to the first object 2 and, for example, is generally less than 3 degrees for all the rotational degrees of freedom.

The change in two of the three translational degrees of freedom is of particular interest, wherein the change in the relative position of the reference mark 18 can be ascertained, for example in relation to the first reference system 12, so as to establish for example that too short or too long of an implant 4' has been attached.

After re-recording the reference point 18 while maintaining a similar alignment to the reference location of the object 2 within the context of the tolerance limits, it is then possible to ascertain the changes in two distances, e.g., the change in the previously detected height 28 and distance 30. Based on the newly measured distance 30' and height 28' of the reference point 18, it is possible to establish, for example, that too short an implant has been introduced, or the positioning of the implant within the body structure has been selected so unfavorably that a shortening or lengthening of the body structure (relative to the original structure) has resulted in a direction from the change in said degree of freedom (within the context of the hip joint operation or total hip arthroplasty (THA), this would for example be the length of the leg). It is also possible to ascertain a change along the second distance, perpendicular to the first direction, which within the context of THA affects the ligament tension in the joint, and influences the lever action of the leg.

Figure 4:
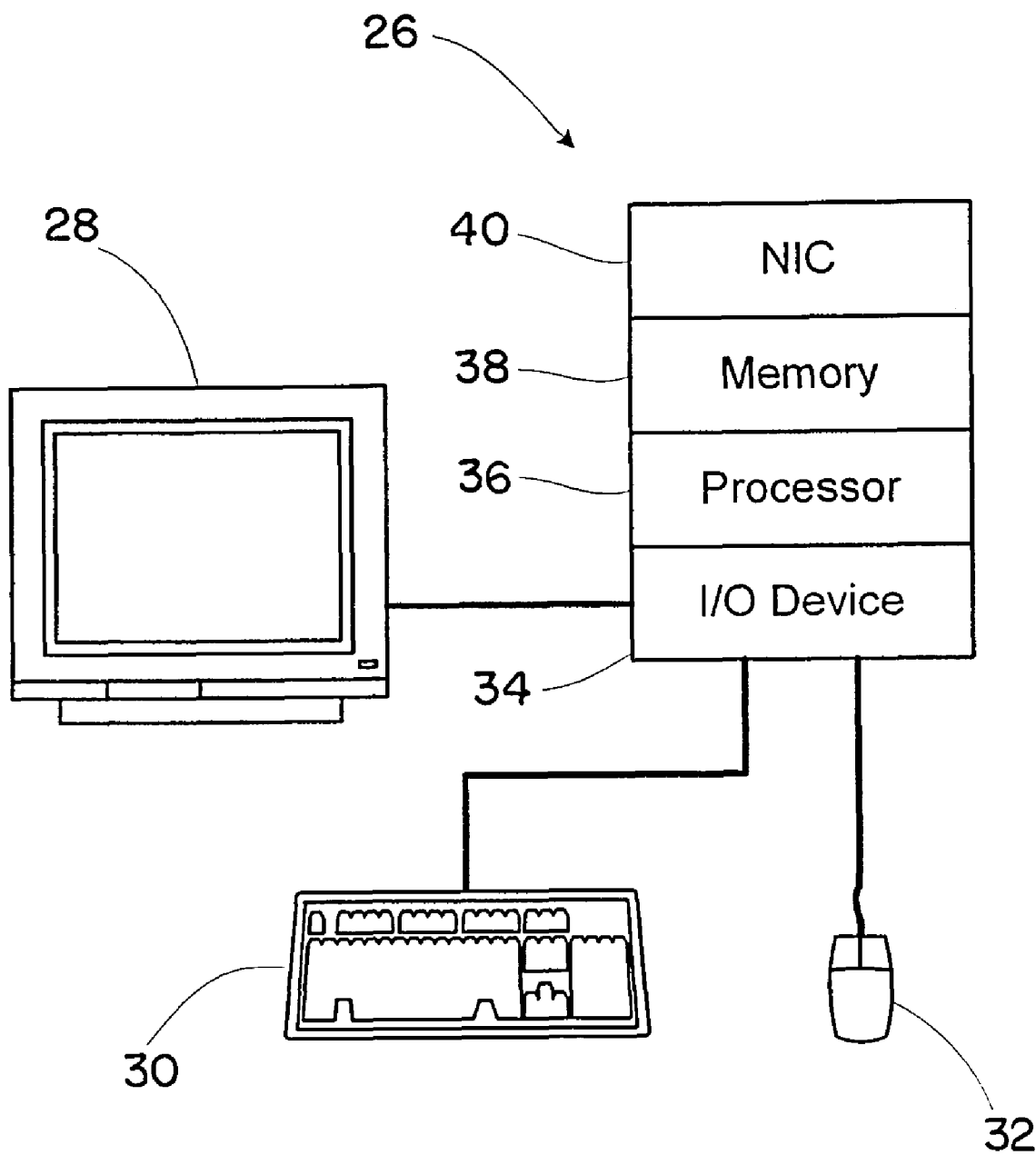
FIG. 4 is a block diagram of an exemplary computer system that may be used to carry out one or more of the methods described herein.

Moving now to FIG. 4 there is shown a block diagram of an exemplary computer 26 that may be used to implement one or more of the methods described herein. The computer 26 may include a display 28 for viewing system information, and a keyboard 30 and pointing device 32 for data entry, screen navigation, etc. A computer mouse or other device that points to or otherwise identifies a location, action, etc., e.g., by a point and click method or some other method, are examples of a pointing device 32. Alternatively, a touch screen (not shown) may be used in place of the keyboard 30 and pointing device 32. The display 28, keyboard 30 and mouse 32 communicate with a processor via an input/output device 34, such as a video card and/or serial port (e.g., a USB port or the like).

A processor 36, such as an AMD Athlon 64® processor or an Intel Pentium IV® processor, combined with a memory 38 execute programs to perform various functions, such as data entry, numerical calculations, screen display, system setup, etc. The memory 38 may comprise several devices, including volatile and non-volatile memory components. Accordingly, the memory 38 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 36 and the memory 38 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 40 allows the computer 26 to communicate with other devices.

A person having ordinary skill in the art of computer programming and applications of programming for computer systems would be able in view of the description provided herein to program a computer system 26 to operate and to carry out the functions described herein. Accordingly, details as to the specific programming code have been omitted for the sake of brevity. Also, while software in the memory 38 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining a dimensional change in a first object, wherein in an initial state said first object is connected to a second object via a joint, and wherein a first reference system is rigidly connected to the second object, comprising:

using a non-invasive coupling device to couple a second reference system to the first object;

ascertaining and/or storing a first location corresponding to a location of the second reference system relative to the first reference system, and a second location corresponding to a location between at least one reference point on the first object relative to the first reference system, wherein ascertaining the second location includes using a pointer to ascertain the second location;

separating the first object from the second object at the joint;

altering the first object;

re-assembling the altered first object and the second object to form the joint, wherein the first location is used to align the altered first object to the second object;

after alignment, ascertaining or storing a third location corresponding to a location of the at least one reference point relative to the first reference system; and determining the dimensional change in the first object due to the alteration based on a change in location between the second location and the third location of the at least one reference point.

2. The method according to claim 1, wherein coupling the second reference system to the first object includes indirectly coupling the second reference system to the first object.

3. The method according to claim 1, wherein using the non-invasive coupling device includes using a belt or elastic strip as the coupling device.

4. The method according to claim 1, wherein coupling the second reference system to the first object includes coupling the second reference system on a mantle that surrounds the first object.

5. The method according to claim 1, wherein ascertaining or storing the first, second and third locations includes using a navigation system to ascertain said locations.

6. The method according to claim 1, wherein the joint is a ball joint.

7. The method according to claim 1, wherein altering the first object includes at least one of cutting or rasping the first object, or introducing or attaching an implant, joint implant or femoral head to the first object.

8. The method according to claim 1, wherein determining a dimensional change in the first object includes determining a change in length of the first object.

9. The method according to claim 1, wherein ascertaining or storing the third location includes ascertaining or storing a location of a reference point different from the at least one reference point, said location of the different reference point being relative to the first reference system, said different reference point having a known positional relationship to the at least one reference point, and deducing a location of the at least one reference point relative to the first reference system from the ascertained or stored position of the different reference point and the known positional relationship to the at least one reference point.

* * * * *